United States Patent [19]

Distler et al.

[11] 4,200,582
[45] Apr. 29, 1980

[54] PREPARATION OF α-HYDROXY-β,β-DIMETHYL-γ-BUTYROLACTONE

[75] Inventors: Harry Distler, Bobenheim; Walter Goetze, Dannstadt-Schauernheim, both of Fed. Rep. of Germany

[73] Assignee: BASF Aktiengesellschaft, Fed. Rep. of Germany

[21] Appl. No.: 969,662

[22] Filed: Dec. 15, 1978

[30] Foreign Application Priority Data

Dec. 30, 1977 [DE] Fed. Rep. of Germany ....... 2758883

[51] Int. Cl.² ............................................ C07D 307/58
[52] U.S. Cl. ................................ 260/343.6; 260/465.6
[58] Field of Search ....................................... 260/343.6

[56] References Cited

U.S. PATENT DOCUMENTS

| 2,399,362 | 4/1946 | Lawson et al. | 562/569 |
| 2,702,816 | 2/1955 | Klein et al. | 260/343.6 |
| 2,852,530 | 9/1958 | Ford | 260/465.6 |
| 2,863,878 | 12/1958 | Lynn | 260/465.6 |

OTHER PUBLICATIONS

Ullmanns Encyklopaedie der Technischen Chemie, vol. 18 (1967), p. 205.
Houben-Weyl, Methoden der Organischen Chemie, vol. VI/2, Part 2 (1963), pp. 656–657.

Primary Examiner—Norma S. Milestone
Attorney, Agent, or Firm—Keil & Witherspoon

[57] ABSTRACT

A process for the preparation of α-hydroxy-β,β-dimethyl-γ-butyrolactone (pantolactone) by condensation of formaldehyde with isobutyraldehyde to give hydroxypivalaldehyde, conversion of the latter to its cyanohydrin, and subsequent acid hydrolysis and lactonization, wherein formaldehyde and butyraldehyde are reacted in the presence of a tertiary amine, hydrocyanic acid, at a concentration not exceeding 1% by weight in the reaction mixture, is used to form the cyanohydrin, and the hydrolysis and simultaneous lactonization are carried out with gaseous hydrogen chloride.

1 Claim, No Drawings

PREPARATION OF α-HYDROXY-β,β-DIMETHYL-γ-BUTYROLACTONE

The present invention relates to a novel process for the preparation of α-hydroxy-β,β-dimethyl-γ-butyrolactone by a one-vessel reaction of formaldehyde with isobutyraldehyde in the presence of a tertiary amine, subsequent reaction with hydrocyanic acid and, following this, hydrolysis with hydrogen chloride gas under specific reaction conditions in respect of temperature, reaction time and hydrocyanic acid concentration.

Ullmanns Encyklopädie der technischen Chemie, volume 18, page 205, discloses that formaldehyde can be condensed with isobutyraldehyde to give α,α-dimethyl-β-hydroxypropionaldehyde and that this aldehyde can then be converted by adduct formation with hydrocyanic acid, into the cyanohydrin, from which α-hydroxy-β,β-dimethyl-γ-butyrolactone (pantolactone) is formed by hydrolysis. According to U.S. Pat. No. 2,399,362, the reaction is carried out by reacting formaldehyde and isobutyraldehyde in the presence of an alkali metal cyanide, treating the reaction mixture with bisulfite and hydrolyzing the resulting formisobutyraldol cyanohydrin, and effecting the lactonization, with a strong mineral acid; in the Example, hydrochloric acid is used as the mineral acid. According to U.S. Pat. No. 2,852,530, an alkali metal carbonate is used instead of sodium cyanide for the condensation, the temperature being from 25° to 45° C. The carbonate is then converted to the bicarbonate by adding a mineral acid and the aldolization mixture is reacted with one mole of alkali metal bicarbonate and one mole of alkali metal cyanide per mole of formisobutyraldol at from −5° to +45° C. As indicated in the Example, hydrochloric acid is used for the hydrolysis.

The process of U.S. Pat. No. 2,702,816 relates to the reaction of glycollic acid nitrile with isobutyraldehyde and an alkali metal hydroxide or alkaline earth metal hydroxide at from 5° to 15° C. and to the hydrolysis of the resulting cyanohydrin with a mineral acid. The glycols formed as by-products must be separated off by adding an alkali metal hydroxide to the hydrolysis mixture and then carrying out a steam distillation. The product is then isolated from the residue by treatment with hydrochloric acid, neutralization, filtration, repeated extraction, drying over anhydrous sodium sulfate, filtration and distillation, i.e. by what is, overall, an involved procedure.

According to the process of U.S. Pat. No. 2,863,878, isobutyraldehyde and formaldehyde are reacted at from 0° to 30° C. in the presence of from 0.5 to 5 percent by weight of a basic catalyst, sodium cyanide is added followed, at 0°–30° C., by hydrocyanic acid, and the mixture is neutralized and is then allowed to react with aqueous hydrochloric acid. The above U.S. Patent teaches carrying out the reaction in solution in an alcohol, e.g. methanol (column 1, line 70, to column 2, line 2). It is true that basic catalysts, for example organic amines, triethylamine and quaternary ammonium hydroxides, can also be used but it is stated expressly that sodium hydroxide is preferred. The Examples show that using isobutyraldehyde and formaldehyde as starting materials (Example 1), only sodium hydroxide is used as the catalyst. Examples 2 and 3 show that only when using previously prepared and isolated hydroxypivalaldehyde as the starting material can both sodium hydroxide and triethylamine be used. Hydrocyanic acid must be added at least in the equimolar amount, as an alcoholic solution; however, as shown by Example 1 and by the description (column 2, lines 50–55; column 3, line 29), an excess of hydrocyanic acid is generally used. The patent states, and shows in the Example, that the reaction is advantageously carried out at from 0° to 15° C. The process necessitates eliminating the excess hydrocyanic acid and the solvents and is therefore expensive to operate industrially. If sodium cyanide is used as a reactant or as the catalyst, an auxiliary acid is required to liberate hydrocyanic acid in the reaction mixture. At the end of the reaction, neutral salt solutions are obtained, which contain cyanide ions and which can only be disposed of industrially at considerable expense if the environment is not to be polluted. In this process, only aqueous dilute mineral acids are used for the hydrolysis.

We have found that α-hydroxy-β,β-dimethyl-γ-butyrolactone is obtained in an advantageous manner by condensation of formaldehyde and isobutyraldehyde to give hydroxypivalaldehyde, conversion of the latter to its cyanohydrin, and subsequent acid hydrolysis and lactonization, if, in a first step, formaldehyde and isobutyraldehyde are reacted in the presence of from 0.01 to 0.3 mole of a teritary amine per mole of isobutyraldehyde for from 30 to 50 minutes at from 80° to 95° C., thereafter, in a second step, the reaction mixture thus formed is reacted with hydrocyanic acid for from 60 to 120 minutes at from 20° to 45° C., with the concentration of the hydrocyanic acid not exceeding 1 percent by weight, based on the reaction mixture, during the reaction, and thereafter, in a third step, the resulting reaction mixture is reacted with gaseous hydrogen chloride.

The reaction takes place in accordance with the following equations:

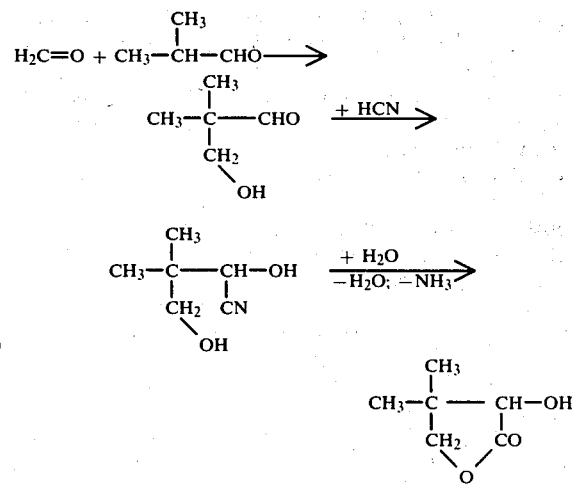

Compared to the conventional processes, the process of the invention gives α-hydroxy-β,β-dimethyl-γ-butyrolactone more simply and more economically, in better yield and higher purity. The process is particularly suitable for continuous operation on an industrial scale, presents no substantial effluent disposal problems and causes less pollution of the environment than the conventional processes. Since, as a rule, the hydrocyanic acid is used in about the stoichiometric amount, based on isobutyraldehyde, the pantolactone solutions obtained are virtually free from cyanide. A further noteworthy advantage of the process according to the invention is the fact that since the excess of hydrocyanic acid is at all times low, a very pure, virtually cyanide-free D,L-pantolactone is formed, which can immediately be converted to pantothenic acid. All these advantages must be regarded as surprising in the light of the prior art.

Formaldehyde can be used as a liquid or a gas, but is in general used in the form of its aqueous solution, advantageously of from 10 to 50 percent strength by weight and preferably of from 30 to 40 percent strength by weight. Hydrocyanic acid is used as the gas or, advantageously, as a liquid. The aldehydes can be employed in the stoichiometric amounts, or with either component in excess, but preferably using from 0.9 to 1.5, especially from 0.9 to 1.1, moles of formaldehyde per mole of isobutyraldehyde.

In the first step, the reaction is carried out in the presence of a tertiary amine in an amount of from 0.01 to 0.3 mole, preferably from 0.06 to 0.1 mole, per mole of isobutyraldehyde. Examples of suitable amines are trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylamine, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N,N-dimethylaminoethanol, N,N-diethylaminoethanol, N,N-dipropylaminoethanol, N-methylpiperidine, N-ethylpiperidine, N-methylpyrrolidine, N-ethylpyrrolidine, M-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine; the trialkylamines mentioned in which each alkyl is of 1 to 4 carbon atoms are particularly advantageous.

The first step of the reaction is carried out continuously at from 80° to 95° C., preferably from 84° to 91° C., under reduced pressure, superatmospheric pressure or, preferably, atmospheric pressure. The reaction time is from 30 to 50, preferably from 35 to 45, minutes. In a preferred embodiment, the first step is divided into two component steps, for example by using two reactors in series; the steps advantageously comprise first (a) a residence time of from 15 to 25 minutes, especially from 18 to 22 minutes, at from 80° to 90° C., especially from 83° to 88° C., and then (b) a residence time of from 15 to 25 minutes, especially from 18 to 22 minutes, at from 85° to 95° C., especially from 88° to 93° C.

In the second step, hydrocyanic acid is added to the starting mixture in such amount that during the reaction the concentration does not exceed 1, advantageously from 0.01 to 1, preferably not more than 0.1, especially from 0.01 to 0.1, and more especially still from 0.01 to 0.06, percent by weight of hydrocyanic acid, based on the reaction mixture. Preferably, water is used as the sole solvent in both the first and the second step, but organic solvents which are inert under the reaction conditions may also be used. Such organic solvents are in principle not essential, but their use may be advisable for technical reasons, for example because of more accurate metering or easier temperature control.

Advantageously, water is used in an amount of from 5 to 50 percent by weight, preferably from 10 to 20 percent by weight, based on isobutyraldehyde. Preferably, water is only introduced into the entire reaction system in the form of the aqueous formaldehyde solution. The hydrocyanic acid and the aldehydes can be employed in about the stoichiometric amount or with either component in excess; preferably, from 0.9 to 1.1 moles, especially from 0.99 to 1.01 moles, of hydrocyanic acid are used per mole of isobutyraldehyde, but more particularly the use of the stoichiometric amounts is preferred. It is possible to add the mixture from the first step to the hydrocyanic acid or, advantageously, to pass the hydrocyanic acid into the mixture. The second step can be carried out under superatmospheric pressure, reduced pressure or, advantageously, atmospheric pressure. The reaction time in the second step is from 60 to 120, preferably from 90 to 110, minutes, and the reaction temperature is from 20° to 45° C., preferably from 20° to 30° C. In a preferred embodiment, the second step is divided into two component steps, for example using two reactors in series, advantageously with first (a) a residence time of from 20 to 70, preferably from 40 to 60, minutes and then (b) a residence time of from 20 to 70, preferably from 40 to 60, minutes at the above temperatures.

A particular characteristic of the process according to the invention is the use of gaseous hydrogen chloride as the hydrolyzing and lactonizing agent in the third reaction step. This step is advantageously carried out continuously at from 50° to 150° C., especially from 75° to 120° C., under superatmospheric pressure or under atmospheric pressure, using from 1.05 to 2, preferably from 1.05 to 1.25, moles of HCl per mole of the cyanohydrin. The residence time is advantageously from 10 to 300, preferably from 30 to 260, minutes. In a preferred embodiment, the third step is divided into two component steps, for example using two reactors in series; the steps advantageously comprise first (a) a residence time of from 1 to 2.5 hours, preferably from 1.8 to 2.2 hours, at from 70° to 100° C., preferably from 75° to 95° C., and then (b) a residence time of from 1 to 2.5 hours, preferably from 1.8 to 2.2 hours, at from 90° to 120°, preferably from 100° to 115° C.

All three steps may be carried out as follows. A mixture of formaldehyde, water, isobutyraldehyde and the tertiary amine is kept at the reaction temperatures concerned for the reaction time concerned. In the second step, the hydrocyanic acid is introduced into the starting mixture, either in portions or, more advantageously continuously, in such a way that the stated hydrocyanic acid concentration is adhered to over the entire reaction time of the second step. The hydrocyanic acid concentrations can be measured throughout, for example by Vollhard titration (Ullmann, loc. cit., volume 5, page 666) or, advantageously, by using a silver-calomel electrode. In the third step, hydrogen chloride gas is added to the mixture. The pantolactone is then isolated from the reaction mixture in the conventional manner, for example by extracting with methyl chloride and distilling the solvent. However, in general—if only for operational and economic reasons—the solution of pantolactone obtained after the third step is directly processed further, for example to pantothenic acid; this is especially advantageous in the case of the process according to the invention, because of the purity of the solutions obtained.

The pantolactone obtainable by the process of the invention is a valuable starting material for the manufacture of drugs and vitamins, especially of pantothenic acid. As regards its use, reference may be made to the above publications and to Ullmanns Encyklopädie der technischen Chemie, volume 18, pages 201–203.

In the Example which follows, parts are by weight.

EXAMPLE

Per hour, 670 parts of 30 percent strength by weight aqueous formaldehyde, 484 parts of isobutyraldehyde and 46.5 parts of triethylamine were passed, at 85° C., through a reactor equipped with a stirrer, reflux condenser and 3 feed vessels. The residence time was 20 minutes. In the next reactor, the reaction mixture was kept at 90° C. for 20 minutes. In the subsequent reactor, 181 parts per hour of hydrocyanic acid were added to the reaction mixture at 25° C., without exceeding a hydrocyanic acid concentration of 0.1% by weight in the reaction space (mean value 0.01–0.05% by weight of HCN). The residence time was 50 minutes. In a finishing reactor, providing a residence time of 50 minutes at 25° C., the hydrocyanic acid concentration of the reaction mixture passing continuously through the reactor fell to less than 4 ppm. In a downstream stirred vessel equipped with a reflux condenser and gas inlet, the reaction mixture was reacted with 317 parts per hour of gaseous HCl at 85° C. After a residence time of 2 hours, the reaction mixture passed into a finishing reactor, where it was kept at 110° C. for 2 hours. Extraction with 700 parts per hour of methylene chloride, and fractional distillation of the extract, gave 836 parts per hour (96% of theory) of pantolacetone, of melting point 88° C. (after recrystallization from methylene chloride).

We claim:

1. A process for the preparation of $\alpha$-hydroxy-$\beta,\beta$-dimethyl-$\gamma$-butyrolacetone by condensation of formaldehyde and isobutyraldehyde, to hydroxypivalaldehyde conversion of the latter to its cyanohydrin, and subsequent acid hydrolysis and lactonization, wherein, in a first step, formaldehyde and isobutyraldehyde are reacted in the presence of from 0.01 to 0.3 mole of a tertiary amine per mole of isobutyraldehyde for from 30 to 50 minutes at from 80° to 95° C., thereafter, in a second step, the reaction mixture thus formed in reacted with hydrocyanic acid for from 60 to 120 minutes at from 20° to 45° C., with the concentration of the hydrocyanic acid not exceeding 1 percent by weight, based on the reaction mixture, during the reaction, and thereafter, in a third step, the resulting mixture is reacted with gaseous hydrogen chloride.

* * * * *